(12) United States Patent
Fenn et al.

(10) Patent No.: US 9,649,325 B2
(45) Date of Patent: May 16, 2017

(54) ESTERIFIED POLYSACCHARIDE OSMOTICS

(75) Inventors: Dominik Fenn, Kaiserslautern (DE); Thomas Fichert, Warendorf (DE); Thomas Schweitzer, Wemmetsweiler (DE); Ingo Bichlmaier, Munich (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 186 days.

(21) Appl. No.: 13/053,128

(22) Filed: Mar. 21, 2011

(65) Prior Publication Data
US 2011/0257124 A1 Oct. 20, 2011

Related U.S. Application Data

(60) Provisional application No. 61/330,479, filed on May 3, 2010.

(30) Foreign Application Priority Data

Mar. 19, 2010 (DE) .................. 10 2010 012 183

(51) Int. Cl.
*A61K 31/718* (2006.01)
*A61M 1/28* (2006.01)
*A61K 31/715* (2006.01)
*A61M 1/16* (2006.01)

(52) U.S. Cl.
CPC .......... *A61K 31/715* (2013.01); *A61K 31/718* (2013.01); *A61M 1/1654* (2013.01); *A61M 1/1666* (2014.02); *A61M 1/287* (2013.01)

(58) Field of Classification Search
None
See application file for complete search history.

(56) References Cited

U.S. PATENT DOCUMENTS

| 4,339,433 | A | * | 7/1982 | Kartinos et al. ........... 424/78.18 |
| 5,436,232 | A | * | 7/1995 | Forster et al. ................ 514/60 |
| 5,789,570 | A | * | 8/1998 | Buchholz et al. ........... 536/107 |
| 5,945,129 | A | * | 8/1999 | Knerr ..................... A61K 33/10 |
| | | | | 424/676 |
| 6,284,140 | B1 | * | 9/2001 | Sommermeyer et al. .... 210/647 |
| 2008/0027374 | A1 | * | 1/2008 | Jensen et al. .................. 604/29 |
| 2009/0306584 | A1 | * | 12/2009 | Schmidtlein et al. ......... 604/28 |

FOREIGN PATENT DOCUMENTS

| DE | 41 23 000 A1 | | 1/1993 |
| DE | 41 23 001 A1 | | 1/1993 |
| EP | 1939219 A1 | * | 2/2008 |
| WO | WO00/57833 | * | 10/2000 | ............... A61J 1/00 |

OTHER PUBLICATIONS

Helmenstine, Anne Marie; "Units of Concentration: Osmolarity and Osmolality"; also available at http://chemistry.about.com/od/solutionsmixtures/a/Osmolarity-And-Osmolality.htm; accessed Jan. 25, 2013.*

* cited by examiner

*Primary Examiner* — Shaojia Anna Jiang
*Assistant Examiner* — Bahar Craigo
(74) *Attorney, Agent, or Firm* — Kilyk & Bowersox, P.L.L.C.

(57) ABSTRACT

The present invention relates to esterified polysaccharide osmotics, use of same, processes for synthesis of same as well as compositions containing same.

7 Claims, 3 Drawing Sheets

ESTERIFIED POLYSACCHARIDE OSMOTICS

CROSS-REFERENCE TO RELATED APPLICATIONS

The present application claims the benefit of U.S. Provisional Patent Application Ser. No. 61/330,479, filed on May 3, 2010, which is hereby incorporated in its entirety by reference thereto. The present application also claims priority to German Patent Application No. 102010012183.5-41, filed on Mar. 19, 2010, which is hereby incorporated in its entirety by reference thereto.

FIELD OF THE INVENTION

The present invention relates to esterified polysaccharide osmotics, their use, processes for synthesis of same and compositions containing same.

BACKGROUND

Osmotically active compounds (osmotics, osmotic agents) are widely used in the pharmaceutical and medical fields. For example, osmotics are used to adjust the tonicity of pharmaceutical drugs, in particular parenteral medications, where the osmotic pressure of a drug is adjusted to be hypotonic, hypertonic or isotonic, depending on how they are administered. For example, the osmotic pressure of a parenteral drug solution can be adjusted to the osmotic pressure of human blood by adding an osmotic agent (iso-osmotic solutions).

Furthermore, osmotics are used in dialysis treatments, in particular in peritoneal dialysis, to withdraw excess water from the dialysis patient.

The peritoneal dialysis process is based on the fact that a solution containing osmotically active compounds is introduced through a catheter into the peritoneal cavity of the dialysis patient. This solution left in the patient's abdominal cavity for a certain period of time (usually a few hours) and develops its osmotic effect there, i.e., endogenous water is withdrawn from the patient's abdominal cavity. After a certain dwell time, the peritoneal dialysis solution which is now dilute is drained out through a catheter.

This principle is used in various peritoneal dialysis treatment methods. For example, the methods of intermittent (IPD), nocturnal intermittent (NIPD), continuous cyclic (CCPD) or continuous ambulant peritoneal dialysis (CAPD) may be used as needed. Instruments used in IPD, NIPD and CCPD support the patient in performing the peritoneal dialysis method. CAPD is a manual method.

The addition of osmotically active compounds in particular should ensure that the osmotic pressure of the peritoneal dialysis solution is high enough during the entire dwell time in the abdominal cavity to withdraw water from the patient, i.e., water is transferred from the patient's circulation into his abdominal cavity (ultrafiltration).

However, because of the transfer of water into the abdominal cavity, the peritoneal dialysis solution introduced there is necessarily diluted. This dilution results in a decline in the concentration of the osmotically active compound and thus also the osmotic pressure of this solution.

If the osmotic pressure of the peritoneal dialysis solution declines because of this dilution, this in turn results in a decline in the transfer of water into the abdominal cavity per occurring per unit of time or it may stop entirely. In these cases, effective removal of water is no longer occurring with a progressively longer dwell time of the peritoneal dialysis solution in the patient's abdominal cavity.

The direction of transfer of water may even be reversed by absorption of osmotically active compounds into the patient's bloodstream, i.e., water is transferred out of the patient's abdominal cavity and into his bloodstream (negative ultrafiltration). This is the case when the dilute peritoneal dialysis solution in the abdominal cavity has a lower osmotic pressure than the endogenous water (e.g., the blood) of the patient.

By adding suitable osmotically active compounds to the peritoneal dialysis solution, the osmotic pressure can be maintained for a treatment time that is suitable for peritoneal dialysis, so there is not an excessive decline in ultrafiltration within the dwell time of the solution in the abdominal cavity. Negative ultrafiltration is thus also largely prevented.

The solutions used in the peritoneal dialysis treatment usually contain sugar monomers or polymers, such as glucose or polyglucose (e.g., starch derivatives), as osmotically active compounds.

EP-B1-0602585 proposes the use of hydroxyethyl starch as an osmotic.

EP-B1-0083360, EP-B2-0115911, EP-B1-0153164 and EP-B1-0207676 relate to solutions for peritoneal dialysis, containing starch hydrolysate-glucose polymers as osmotically active compounds.

DETAILED DESCRIPTION

Figure 1:
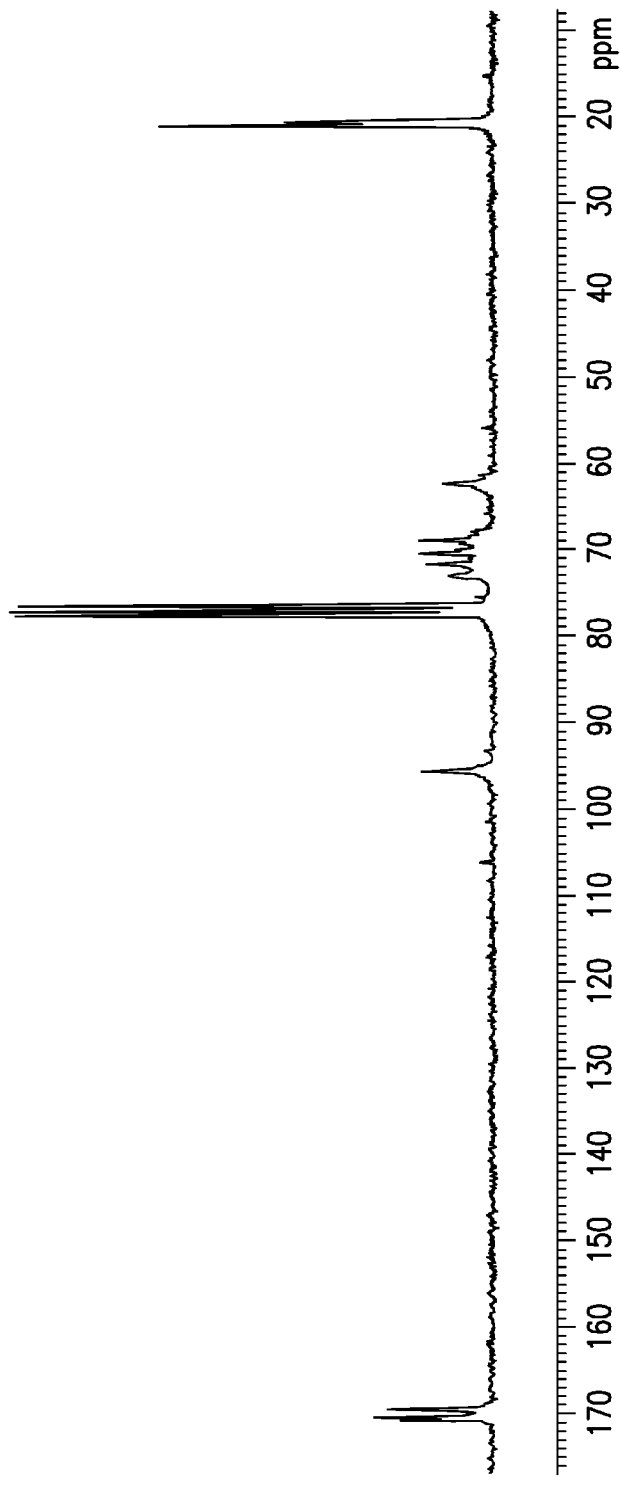
FIG. 1 is a graph showing a CNMR spectrum.

The object of the present invention is in particular to make available osmotics which have a higher osmotic activity than traditional osmotically active compounds and are therefore suitable in particular for use in peritoneal dialysis treatment.

This object is achieved through the subject of the patent claims.

The inventive osmotics are characterized in that, in comparison with traditional osmotics, they have a higher osmotic activity at the same concentration.

This increased osmotic activity leads in particular to removal of water (ultrafiltration) during the dialysis treatment being increased and/or maintained for a long period of time. Thus, there is more effective removal of water in the dialysis treatment when using the inventive osmotics in particular. This may contribute toward shortening of the dialysis treatment time, for example. Alternatively, the concentration of the inventive osmotic may be reduced to achieve the same osmotic activity of a traditional osmotic.

The shortening of the dialysis treatment time and/or the reduction in the reduction in the concentration may in turn lead to a lower incidence of adverse effects in the dialysis patient.

A first subject of this invention concerns polysaccharides containing monosaccharide monomers, which are esterified at least partially with a dicarboxylic acid and/or tricarboxylic acid esterified, for use as an osmotic.

Through esterification of the polysaccharide with a dicarboxylic acid and/or tricarboxylic acid, deprotonatable side chains, which are thus also anionically charged, are introduced into the polysaccharide.

It has been found that by introducing these deprotonatable and/or anionic side chains, the efficiency of the peritoneal dialysis treatment is improved by increased ultrafiltration.

For the purpose of this description, the term "polysaccharide" comprises compounds containing at least ten monosaccharide monomers (Pure & Applied Chemistry, 1995, 67, 1360).

In the sense of this description, the terms "esterified" and "ester" comprise compounds which have the structural unit the structural unit —C(=O)—O— (Pure & Applied Chemistry, 1995, 67, 1334).

In a preferred embodiment, the dicarboxylic acid is a physiological dicarboxylic acid and the tricarboxylic acid is a physiological tricarboxylic acid.

In the sense of this description, the term "physiological dicarboxylic acid" and/or "physiological tricarboxylic acid" comprise(s) dicarboxylic acids and/or tricarboxylic acids, which occur in the human metabolism. Examples that can be mentioned here include the physiological dicarboxylic and tricarboxylic acids of the Krebs cycle.

In the sense of this description, the term "dicarboxylic acid" stands for an organic compound having two acid groups (carboxyl groups, —COOH), and the term "tricarboxylic acid" stands for an organic compound having three acid groups. The acid groups may be uncharged, i.e., present as —COOH (carboxyl) or anionic, i.e., deprotonated as —COO$^-$ (carboxylate).

In the case when the acid group is present as an anionic carboxylate, it may form a salt with a cationic counterion (e.g., sodium, potassium, calcium, magnesium cation).

The dicarboxylic acid is preferably selected from the group including oxalic acid, oxalacetic acid, ketoglutaric acid, glutamic acid, aspartic acid, fumaric acid, maleic acid, malic acid, malonic acid, succinic acid, glutaric acid, adipic acid, pimelic acid, suberic acid, azelaic acid, sebacic acid. In another preferred embodiment, the dicarboxylic acid is oxalic acid, glutamic acid, aspartic acid, maleic acid or succinic acid. Maleic acid and succinic acid are preferred in particular.

The tricarboxylic acid is preferably citric acid or isocitric acid, in particular citric acid.

The inventive polysaccharide may be composed of the same or different monosaccharide monomers. The inventive polysaccharide is preferably composed of the same monosaccharide monomers. Glucose is preferred in particular.

However, the polysaccharide may be composed of monosaccharide monomers other than glucose and/or fructose. Those skilled in the art are familiar with typical monosaccharide monomers.

The monosaccharide monomers in the inventive polysaccharide are preferably linked by glycosidic bonds.

The inventive polysaccharide may be crosslinked. Typical crosslinking agents are well-known to those skilled in the art. Epichlorohydrin and diisocyanate compounds may be mentioned here as examples. It is preferred in particular for the inventive polysaccharide not to be crosslinked.

The average molecular weight of the inventive polysaccharide is preferably 2000 to 30,000 g/mol, more preferably 2500 to 26,000 g/mol, even more preferably 3000 to 22,000 g/mol, even more preferably 3500 to 20,000 g/mol, most preferably 4000 to 18,000 g/mol and in particular 5000 to 15,000 g/mol.

In another preferred embodiment, the average molecular weight of the inventive polysaccharide is 15,000 to 25,000 g/mol, in particular 18,000 to 22,000 g/mol.

The inventive polysaccharide preferably has an average degree of polymerization of 10 to 170, more preferably 11 to 130, even more preferably 12 to 100, most preferably 13 to 80 and in particular 14 to 50.

In another preferred embodiment, the average degree of polymerization of the inventive polysaccharide is 80 to 140, preferably 85 to 135, more preferably 90 to 130, most preferably 95 to 125 and in particular 100 to 120.

A 7.5 weight percent aqueous solution of the inventive polysaccharide preferably has a theoretical osmolarity of >11.9 mosm/L, more preferably greater than ≥12.5 mosm/L, even more preferably greater than ≥13.0 mosm/L, most preferably greater than ≥13.5 mosm/L and in particular greater than ≥14.0 mosm/L.

For the purpose of this description, the term "theoretical osmolarity" stands for theoretically calculated osmolarity. Methods of calculating this value are familiar to those skilled in the art.

In a preferred embodiment, the colloid osmotic pressure of a 7.5 weight percent solution of the inventive polysaccharide is ≥50 mosm/L or ≥60 mosm/L, more preferably ≥70 mosm/L or ≥80 mosm/L, even more preferably ≥90 mosm/L or ≥100 mosm/L, most preferably ≥110 mosm/L or ≥120 mosm/L and in particular ≥130 mosm/L or ≥140 mosm/L.

In another preferred embodiment, the colloid osmotic pressure of a 7.5 weight percent solution of the inventive polysaccharide is ≥150 mosm/L or ≥160 mosm/L, more preferably ≥170 mosm/L or ≥180 mosm/L, even more preferably ≥190 mosm/L or ≥200 mosm/L, most preferably ≥210 mosm/L or ≥220 mosm/L and in particular ≥230 mosm/L or ≥240 mosm/L.

In another preferred embodiment, the colloid osmotic pressure of a 7.5 weight percent solution of the inventive polysaccharide is 50 to 500 mosm/L, more preferably 75 mosm/L to 400 mosm/L, even more preferably 100 to 300 mosm/L, most preferably 110 mosm/L to 275 mosm/L and in particular 120 mosm/L to 250 mosm/L.

In another preferred embodiment, the colloid osmotic pressure of a 7.5 weight percent solution of the inventive polysaccharide is 100 to 500 mosm/L, more preferably 100 mosm/L to 400 mosm/L, even more preferably 100 to 350 mosm/L, most preferably 100 mosm/L to 325 mosm/L and in particular 100 mosm/L to 290 mosm/L.

For the purpose of this description, the term "colloid osmotic pressure" stands for the experimentally measured osmotic pressure of the solution, which is comprised of the osmotic and oncotic pressure. Those skilled in the art are familiar with suitable methods of experimental determination of this value.

The osmolality of a 7.5 weight percent aqueous solution of the inventive polysaccharide is preferably >16 mosm/kg, more preferably ≥18 mosm/kg, even more preferably ≥20 mosm/kg, most preferably ≥22 mosm/kg and in particular ≥25 mosm/kg.

For the purpose of this description, the term "osmolality" stands for the osmolality of the solution, which is determined experimentally based on the reduction in freezing point. Those skilled in the art are familiar with methods of determining the reduction in freezing point.

The osmolarity of a 7.5 weight percent aqueous solution of the inventive polysaccharide determined experimentally based on the reduction in freezing point preferably amounts to >15 mosm/L, more preferably ≥17 mosm/L, even more preferably ≥19 mosm/L, most preferably ≥21 mosm/L and in particular ≥23 mosm/L. The inventive polysaccharide is esterified with the dicarboxylic acids and/or tricarboxylic acids described above. The inventive polysaccharide has a degree of substitution of 0.01 to 3, preferably 0.05 to 2.5, more preferably 0.1 to 2, most preferably 0.25 to 1.5 and in particular 0.5 to 1.

In another preferred embodiment, the inventive polysaccharide has a degree of substitution of 0.02±0.01 or 0.05±0.025, more preferably 0.1±0.05, even more preferably 0.5±0.25, most preferably 1±0.5 and in particular 1.5±0.75.

In an especially preferred embodiment, the inventive polysaccharide has a degree of substitution of 0.02±0.005 or 0.05±0.0125, more preferably 0.1±0.025, even more preferably 0.5±0.125, most preferably 1±0.25 and in particular 1.5±0.375.

The inventive polysaccharide is preferably suitable as an osmotic agent for adjusting the tonicity of pharmaceutical drugs, in particular drug solutions for parenteral administration.

In a preferred embodiment, the inventive polysaccharide is used in a dialysis treatment, preferably in hemodialysis and/or peritoneal dialysis treatment.

The inventive polysaccharide is suitable in particular for use in peritoneal dialysis treatment.

Another subject of this invention relates to a method for synthesis of the inventive polysaccharide, comprising the steps
 a. Mixing a polysaccharide with a first organic solvent,
 b. Mixing the dispersion or solution obtained in step a. with a dicarboxylic acid anhydride and/or a tricarboxylic acid anhydride.

The polysaccharide used in step a. is preferably degraded starch.

In a preferred embodiment, a catalyst which accelerates the esterification reaction is added to the solution or dispersion obtained in step b. This catalyst is preferably a nucleophilic catalyst, preferably 4-(dimethylamino)pyridine (DMAP). Those skilled in the art are familiar with other catalysts having a similar activity.

In addition, a base may also be added, preferably an amine base, such as triethylamine. Those skilled in the art are familiar with other amine bases.

The catalyst is preferably added in catalytic amounts, i.e., the substance quantity ratio of catalyst (e.g., DMAP) to acid anhydride is preferably ≤1:10 or ≤1:25, more preferably ≤1:50 or ≤1:75, even more preferably ≤1:75 or ≤1:100, most preferably ≤1:250 and in particular ≤1:500.

After step b., the reaction mixture may be stirred at an elevated temperature. The temperature is preferably 40 to 80° C., more preferably 50 to 70° C., even more preferably 55 to 65° C. and in particular 60° C.

In a preferred embodiment, the reaction mixture obtained in step b. is stirred for 1 to 12 hours, more preferably for 2 to 8 hours, even more preferably for 4 to 6 hours and in particular for 5 hours.

The substance quantity ratio of acid anhydride to polysaccharide is preferably 0.1 to 5 mol/AGU, more preferably 0.2 to 4 mol AGU, even more preferably 0.3 to 3 mol/AGU, most preferably 0.4 to 2 mol/AGU and in particular 0.5 to 1 mol/AGU.

In another preferred embodiment, the substance quantity ratio is 0.1 to 2.5 mol/AGU, more preferably 0.2 to 1.75 mol/AGU, even more preferably 0.3 to 1.5 mol/AGU, most preferably 0.4 to 1.25 mol/AGU and in particular 0.5 to 0.75 mol/AGU.

In the sense of this description, the abbreviation "AGU" stands for "anhydrous glucose unit." Those skilled in the art are familiar with this standard term.

The inventive polysaccharide may be separated from the solution or dispersion by precipitation, where precipitation may be induced by adding a second organic solvent.

The precipitation is preferably performed due to the fact that the inventive polysaccharide has a higher solubility in the first organic solvent than in the second organic solvent or in a mixture of the first and second organic solvents.

The first organic solvent may be any organic solvent, in which the polysaccharide can be dissolved or dispersed. In a preferred embodiment, the first organic solvent is dimethyl sulfoxide or dimethylacetamide or a mixture thereof. Dimethyl sulfoxide is preferred in particular.

The second organic solvent may be any organic solvent, in which the inventive polysaccharide has a lower solubility than in the first organic solvent.

The second organic solvent is preferably an alcoholic solvent—preferably methanol, ethanol, propanol, isopropanol or butanol—or a ketone solvent—preferably acetone or ethyl methyl ketone. Ethanol in particular is preferred as the alcoholic solvent. Acetone in particular is preferred as the ketone solvent.

If dimethyl sulfoxide is used as the first organic solvent, it is preferred in particular for ethanol to be used as the second organic solvent for the precipitation.

If dimethylacetamide is used as the first organic solvent, it is preferred in particular for acetone to be used as the second organic solvent for the precipitation.

After precipitation of the inventive polysaccharide, the separation is preferably performed by filtering the precipitated precipitate.

The filtered precipitate is preferably dried. This drying step is preferably performed at an elevated temperature (preferably 40° C.) and at a reduced pressure (preferably in vacuo).

In an especially preferred embodiment, the method for synthesis of the inventive polysaccharides comprises the following steps:
  Mixing a polysaccharide—preferably degraded starch—with dimethyl sulfoxide and/or dimethylacetamide,
  Adding dicarboxylic acid anhydride and/or tricarboxylic acid anhydride, a nucleophilic catalyst and optionally an amine base,
  Stirring the mixture at a temperature of 20 to 80° C. for 2 to 12 hours,
  Adding an alcoholic solvent or a ketone solvent, to induce precipitation of the esterified polysaccharide,
  Filtering the precipitate and
  Drying the precipitate.

In a particularly preferred embodiment, the method for synthesis of the inventive polysaccharide comprises the following steps:
  Mixing a polysaccharide with dimethyl sulfoxide or dimethylacetamide,
  Adding dicarboxylic acid anhydride and/or tricarboxylic acid anhydride, DMAP and optionally triethylamine,
  Stirring the mixture for 3 to 7 hours at a temperature of 50 to 70° C.,
  Adding ethanol, if the solvent is dimethyl sulfoxide or adding acetone, if the solvent is dimethylacetamide, to induce precipitation of the inventive polysaccharide,
  Filtering the precipitate and
  Drying the precipitate.

Another subject of this invention relates to dialysis solutions containing at least one inventive polysaccharide.

In a preferred embodiment, the inventive dialysis solution is a hemodialysis solution or a peritoneal dialysis solution. The inventive dialysis solution is in particular a peritoneal dialysis solution.

Dosage forms, which are used in dialysis treatment, are preferably concentrates in multicomponent systems or ready-to-use dialysis solutions.

For the purposes of this invention, the term "dialysis solution" comprises a ready-to-use dosage form for dialysis treatment, i.e., a liquid preparation, which is suitable for administration as such. In particular the dialysis solution need not be diluted and/or mixed with other preparations before administration.

In contrast with the dialysis solutions described above, concentrates which may be present in liquid, semisolid or solid form are diluted with water or aqueous solutions or are dissolved in water or aqueous solutions before being administered. Similarly, the components of a multicomponent system must be mixed together before being administered, to yield a ready-to-use dialysis solution. Concentrates and multicomponent systems may thus be regarded as a precursor to the inventive dialysis solution.

The inventive dialysis solution is preferably a hemodialysis solution or a peritoneal dialysis solution. Hemodialysis solutions and peritoneal dialysis solutions usually contain electrolytes in a concentration, which corresponds essentially to the plasma electrolyte concentration. Electrolytes usually include sodium, potassium, calcium, magnesium and chloride ions.

Dialysis solutions usually have a physiologically tolerable pH. This is preferably achieved by buffers (buffer systems), which may also contribute to the total electrolyte content. The buffers are preferably bicarbonate, lactate or pyruvate.

Furthermore, dialysis solutions usually have a physiologically tolerable osmolarity. This is usually achieved through the electrolytes contained in the dialysis solution and inventive polysaccharides, which are physiologically tolerable as osmotically active compounds (osmotics) in the desired concentration.

The inventive dialysis solution has an osmolarity in the range of preferably 200 to 550 mosm/L.

If the inventive dialysis solution is a hemodialysis solution, the osmolarity is preferably 200 to 350 mosm/L or 210 to 340 mosm/L, more preferably 220 to 330 mosm/L, even more preferably 230 to 320 mosm/L, most preferably 240 to 310 mosm/L and in particular 250 to 300 mosm/L. Those skilled in the art are familiar with methods of measuring the osmolarity and the osmotic pressure. For example, these pressures can be determined with the help of a membrane osmometer or by other suitable measurement methods.

If the inventive dialysis solution is a peritoneal dialysis solution, the osmolarity is preferably 200 to 570 mosm/L or 210 to 560 mosm/L, more preferably 220 to 550 mosm/L, even more preferably 230 to 540 mosm/L, most preferably 240 to 530 mosm/L and in particular 250 to 520 mosm/L. In a preferred embodiment, the osmolarity is 250±50 mosm/L or 250±45 mosm/L, more preferably 250±35 mosm/L, even more preferably 250±25 mosm/L, most preferably 250±15 mosm/L, and in particular 250±10 mosm/L. In another preferred embodiment, the osmolarity 300±50 mosm/L or 300±45 mosm/L, more preferably 300±35 mosm/L, even more preferably 300±25 mosm/L, most preferably 300±15 mosm/L and in particular 300±10 mosm/L. In another preferred embodiment, the osmolarity is 350±50 mosm/L or 350±45 mosm/L, more preferably 350±35 mosm/L, even more preferably 350±25 mosm/L, most preferably 350±15 mosm/L and in particular 300±10 mosm/L. In another preferred embodiment, the osmolarity is 400±50 mosm/L or 400±45 mosm/L, more preferably 400±35 mosm/L, even more preferably 400±25 mosm/L, most preferably 400±15 mosm/L and in particular 300±10 mosm/L. In another preferred embodiment, the osmolarity is 450±50 mosm/L or 450±45 mosm/L, more preferably 450±35 mosm/L, even more preferably 450±25 mosm/L, most preferably 450±15 mosm/L and in particular 450±10 mosm/L. In another preferred embodiment, the osmolarity is 500±50 mosm/L or 500±45 mosm/L, more preferably 500±35 mosm/L, even more preferably 500±25 mosm/L, most preferably 500±15 mosm/L and in particular 500±10 mosm/L.

The inventive dialysis solution has a pH of preferably 4.0 to 8.0, more preferably 4.2 to 7.5, even more preferably 4.4 to 6.8, most preferably 4.6 to 6.0 or 4.8 to 5.5 and in particular 5.0 to 5.2 or 5.0±0.1, measured at room temperature (20 to 23° C.). In a preferred embodiment, pH is 4.8±1.0 or 4.8±0.8, more preferably 4.8±0.7 or 4.8±0.6, even more preferably 4.8±0.5 or 4.8±0.4, most preferably 4.8±0.3 or 4.8±0.2 and in particular 4.8±0.1. In another preferred embodiment, the pH is 5.0±1.0 or 5.0±0.8, more preferably 5.0±0.7 or 5.0±0.6, even more preferably 5.0±0.5 or 5.0±0.4, most preferably 5.0±0.3 or 5.0±0.2 and in particular 5.0±0.1. In another preferred embodiment, the pH is 5.2±1.0 or 5.2±0.8, more preferably 5.2±0.7 or 5.2±0.6, even more preferably 5.2±0.5 or 5.2±0.4, most preferably 5.2±0.3 or 5.2±0.2 and in particular 5.2±0.1. In another preferred embodiment, the pH is 5.5±1.0 or 5.5±0.8, more preferably 5.5±0.7 or 5.5±0.6, even more preferably 5.5±0.5 or 5.5±0.4, most preferably 5.5±0.3 or 5.5±0.2 and in particular 5.5±0.1. In another preferred embodiment, the pH is 6.0±1.0 or 6.0±0.8, more preferably 6.0±0.7 or 6.0±0.6, even more preferably 6.0±0.5 or 6.0±0.4, most preferably 6.0±0.3 or 6.0±0.2 and in particular 6.0±0.1. In another preferred embodiment, the pH is 6.5±1.0 or 6.5±0.8, more preferably 6.5±0.7 or 6.5±0.6, even more preferably 6.5±0.5 or 6.5±0.4, most preferably 6.5±0.3 or 6.5±0.2 and in particular 6.5±0.1. In another preferred embodiment, the pH is 7.0±1.0 or 7.0±0.8, more preferably 7.0±0.7 or 7.0±0.6, even more preferably 7.0±0.5 or 7.0±0.4, most preferably 7.0±0.3 or 7.0±0.2 and in particular 7.0±0.1. In another preferred embodiment, the pH is 7.4±1.0 or 7.4±0.8, more preferably 7.4±0.7 or 7.4±0.6, even more preferably 7.4±0.5 or 7.4±0.4, most preferably 7.4±0.3 or 7.4±0.2 and in particular 7.4±0.1. In another preferred embodiment, the pH is 8.0±1.0 or 8.0±0.8, more preferably 8.0±0.7 or 8.0±0.6, even more preferably 8.0±0.5 or 8.0±0.4, most preferably 8.0±0.3 or 8.0±0.2 and in particular 8.0±0.1.

The inventive dialysis solution contains one or more (e.g., two, three, four or five) inventive polysaccharides, where the inventive polysaccharides are defined as above.

The inventive dialysis solution contains the inventive polysaccharide in a total concentration of preferably 0.001 mM to 10 M or 0.01 to 1.0 M, more preferably 0.10 to 500 mM, even more preferably 1.0 to 250 mM, most preferably 10 to 100 mM and in particular 25 to 90 mM. In a preferred embodiment, the total concentration is 25±24 mM, more preferably 25±20 mM, even more preferably 25±15 mM, most preferably 25±10 mM and in particular 25±5 mM. In another preferred embodiment, the total concentration is 50±25 mM, more preferably 50±20 mM, even more preferably 50±15 mM, most preferably 50±10 mM and in particular 50±5 mM. In another preferred embodiment, the total concentration is 75±25 mM, more preferably 75±20 mM, even more preferably 75±15 mM, most preferably 75±10 mM and in particular 75±5 mM. In another preferred embodiment, the total concentration is 100±25 mM, more preferably 100±20 mM, even more preferably 100±15 mM, most preferably 100±10 mM and in particular 100±5 mM. In another preferred embodiment, the total concentration is 200±25 mM, more preferably 200±20 mM, even more preferably 200±15 mM, most preferably 200±10 mM and in particular 200±5 mM. The total concentration is preferably calculated based on the average molecular weight of the inventive polysaccharide.

The inventive dialysis solution contains the inventive polysaccharide in a total mass concentration of preferably 0.01 g/L to 1.0 kg/L, more preferably 0.1 to 750 g/L, even more preferably 1.0 to 500 g/L, most preferably 10 to 250 g/L, and in particular 100 to 200 g/L. In a preferred embodiment, the total mass concentration is 25±24 g/L, more preferably 25±20 g/L, even more preferably 25±15 g/L, most preferably 25±10 g/L and in particular 25±5 g/L. In another preferred embodiment, the total mass concentration is 50±25 g/L, more preferably 50±20 g/L, even more preferably 50±15 g/L, most preferably 50±10 g/L and in particular 50±5 g/L. In another preferred embodiment, the total mass concentration is 75±25 g/L, more preferably 75±20 g/L, even more preferably 75±15 g/L, most preferably 75±10 g/L and in particular 75±5 g/L. In another preferred embodiment, the total mass concentration 100±25 g/L, more preferably 100±20 g/L, even more preferably 100±15 g/L, most preferably 100±10 g/L and in particular 100±5 g/L. In another preferred embodiment, the total mass concentration is 200±25 g/L, more preferably 200±20 g/L, even more preferably 200±15 g/L, most preferably 200±10 g/L and in particular 200±5 g/L.

The inventive dialysis solution may also contain other osmotically active substances such as glucose, polyglucose, crosslinked glucose or polyglucose, mannitol or glycerol.

The inventive dialysis solution preferably contains one or more electrolytes.

In the sense of this invention, the term "electrolyte" stands for a substance that contains free ions and has electric conductivity. The electrolyte preferably dissociates completely into cations and anions without essentially altering the pH of an aqueous composition. This property differentiates electrolytes from buffer substances. The electrolytes are preferably in a concentration which results in an essentially complete dissociation in water.

Preferred electrolytes are selected from the group of alkali metals, such as $Na^+$ and $K^+$ and the alkaline earth metals, such as $Ca^{2+}$ and $Mg^{2+}$. A preferred anion is $Cl^-$.

The inventive dialysis solution may contain other anions, such as bicarbonate, dihydrogen phosphate, hydrogen phosphate, phosphate, acetate, lactate and pyruvate. However, because of their buffer capacity, these anions (in suitable combinations with cations) are not referred to as electrolytes in the sense of this invention but instead as buffers.

In a preferred embodiment, the inventive dialysis solution contains $Na^+$ ions. The concentration of $Na^+$ ions is preferably 10 to 200 mM or 50 to 190 mM, more preferably 100 to 180 mM or 110 to 170 mM, even more preferably 115 to 165 mM or 120 to 160 mM, most preferably 125 to 155 mM and in particular 130 to 150 mM. In another preferred embodiment, the inventive dialysis solution does not contain any $Na^+$ ions.

In a preferred embodiment, the inventive dialysis solution contains $K^+$ ions. The concentration of $K^+$ ions is preferably 0.10 to 20 mM, more preferably 0.25 to 15 mM, even more preferably 0.50 to 10 mM, most preferably 0.75 to 7.5 mM and in particular 1.0 to 5.0 mM. In another preferred embodiment, the concentration of $K^+$ ions is 1.0±0.75, 2.0±0.75, 3.0±0.75, 4.0±0.75 or 5.0±0.75 mM and in particular 1.0±0.50, 2.0±0.50, 3.0±0.50, 4.0±0.50 or 5.0±0.50. In another preferred embodiment, the inventive dialysis solution does not contain any $K^+$ ions.

In a preferred embodiment, the inventive dialysis solution contains $Ca^{2+}$ ions. The concentration of $Ca^{2+}$ ions is preferably 0.1 to 3 mM, more preferably 0.25 to 2.75 mM, even more preferably 0.5 to 2.5 mM, most preferably 0.75 to 2.25 mM and in particular 1 to 2 mM. In another preferred embodiment, the concentration of $Ca^{2+}$ ions is 0.25, 0.5, 0.75, 1, 1.25, 1.5, 1.75 or 2 mM. In another preferred embodiment, the inventive dialysis solution does not contain any $Ca^{2+}$ ions.

In a preferred embodiment, the inventive dialysis solution contains $Mg^{2+}$ ions. The concentration of $Mg^{2+}$ ions is preferably 0.01 to 1 mM, more preferably 0.05 to 0.75 mM, even more preferably 0.1 to 0.5 mM, most preferably 0.15 to 0.4 mM and in particular 0.2 to 0.3 mM. In another preferred embodiment, the concentration of $Mg^{2+}$ ions is 0.05, 0.075, 0.1, 0.2, 0.25, 0.50 or 0.75 mM. In another preferred embodiment, the inventive dialysis solution does not contain any $Mg^{2+}$ ions.

In a preferred embodiment, the inventive dialysis solution contains $Cl^-$ ions. The concentration of $Cl^-$ ions is preferably 10 to 300 mM, more preferably 25 to 250 mM, even more preferably 50 to 200 mM, most preferably 75 to 150 mM and in particular 80 to 125 mM. In another preferred embodiment, the concentration of $Cl^-$ ions is 100±50 mM, more preferably 100±25 mM, most preferably 100±10 mM and in particular 96±4 mM. In another preferred embodiment, the inventive dialysis solution does not contain any $Cl^-$ ions.

The inventive dialysis solution contains preferably one or more buffers.

Those skilled in the art are familiar with suitable buffers. Buffers usually include lactate, bicarbonate, carbonate, dihydrogen phosphate, hydrogen phosphate, phosphate, pyruvate, citrate, isocitrate, succinate, fumarate, acetate and lactate salts. Those skilled in the art know that the corresponding cation of the anions listed above is a component of the buffer used to adjust the pH (e.g., $Na^\oplus$ as a component of the buffer $NaHCO_3$). However, if the buffer salt dissociates in water, it also has the effect of an electrolyte. For the purposes of this description, the concentrations of cations or anions and the total concentration of ion is calculated regardless of whether they are used as a component of electrolytes, buffers or other compounds (e.g., as a salt of the inventive polysaccharide).

In a preferred embodiment, the buffer contains bicarbonate. Bicarbonate is a buffer system that is tolerated well and is in equilibrium with carbonate in an alkaline medium and is in equilibrium with $H_2CO_3$ and/or $CO_2$ in an acidic medium. In addition to bicarbonate, other buffer systems can also be used, if they have a buffering effect in the pH range of pH 4 to pH 8, more preferably in the range of pH 5 to pH 7.6 and in particular in the range of pH 7.6, 7.4, 7.2 and/or 7.0, e.g., including compounds that can be metabolized to bicarbonate in the body, such as lactate or pyruvate.

In another preferred embodiment, the buffer contains the salt of a weak acid, preferably lactate. The acid strength ($pK_s$) of the weak acid is preferably ≤5. The buffer may also be a mixture of substances having a buffer effect, e.g., a mixture containing bicarbonate and a salt of a weak acid (e.g., lactate). A low bicarbonate concentration has the advantage that the $CO_2$ pressure in the container is low.

In a preferred embodiment, the inventive dialysis solution is buffered by bicarbonate. The bicarbonate concentration is preferably 1.0 to 200 mM, more preferably 2.5 to 150 mM, even more preferably 5 to 100 mM, most preferably 5 to 75 mM or 10 to 50 mM and in particular 20 to 30 mM. In another preferred embodiment, the bicarbonate concentration is 25 mM. In another preferred embodiment, the inventive dialysis solution does not contain any bicarbonate.

In a preferred embodiment, the inventive dialysis solution is buffered by lactate. The lactate concentration is preferably 1.0 to 200 mM, more preferably 2.5 to 150 mM, even more preferably 5 to 100 mM, most preferably 10 to 50 mM or 10 to 25 mM and in particular 15 mM. In another preferred embodiment, the inventive dialysis solution does not contain any lactate.

In a preferred embodiment, the inventive dialysis solution is buffered by acetate. The acetate concentration is preferably 1.0 to 100 mM, more preferably 1.0 to 50 mM, even more preferably 1.0 to 25 mM, most preferably 1.0 to 10 mM or 2.0 to 7.5 mM and in particular 2.5 to 7.0 mM. In another preferred embodiment, the inventive dialysis solution does not contain any acetate.

The total volume of dialysis solution is not limited. The volume is usually several liters (suitable volume for administration to a patient) up to a few hundred liters (suitable storage volume for more than one patient).

As already explained above, the term "dialysis solution" in the sense of this invention is understood to be a ready-to-use dialysis solution, i.e., the dialysis solution may be used directly for the dialysis treatment (hemodialysis or peritoneal dialysis).

In a preferred embodiment, the inventive dialysis solution is a peritoneal dialysis solution as described below.

The peritoneal dialysis solution is adjusted biochemically so that it essentially corrects the metabolic acidosis associated with renal failure. The peritoneal dialysis solution preferably contains bicarbonate in approximately physiological concentrations. In a preferred embodiment, the peritoneal dialysis solution contains bicarbonate in a concentration of approximately 20 to 30 mM. In another preferred embodiment, the peritoneal dialysis solution has a bicarbonate concentration of 25 mM.

Furthermore, the peritoneal dialysis solution preferably contains carbon dioxide with a partial pressure ($pCO_2$) of less than 60 mmHg. In a preferred embodiment, the $pCO_2$ of the peritoneal dialysis solution is essentially the same as the $pCO_2$ measured in the blood vessels.

Furthermore, the peritoneal dialysis solution preferably has a pH of approximately 7.4. Therefore, the peritoneal dialysis solution is a physiologically tolerable solution.

The peritoneal dialysis solution preferably contains a weak acid with a $pK_s$ of ≤5. The weak acids are preferably compounds which occur as physiological metabolites in the glucose metabolism. The weak acid is preferably selected from the group consisting of lactate, pyruvate, citrate, isocitrate, ketoglutarate, succinate, fumarate, malate and oxaloacetate. These acids may be present in the peritoneal dialysis solution either alone or as a mixture. The weak acids are preferably present in the peritoneal dialysis solution in a concentration of 10 to 20 meq/L and essentially as sodium salts. In the peritoneal dialysis solution, the weak acid is preferably present in an amount corresponding to the daily metabolic water production of approximately 1 meq/kg per day.

The peritoneal dialysis solution contains at least one inventive polysaccharide as defined above.

The inventive peritoneal dialysis solution preferably contains a concentration of bicarbonate and has a $pCO_2$, such as that measured in healthy non-renally-insufficient patients. The weak acid diffuses along the concentration gradient from the dialysis solution into the blood of the dialysis patient and thus corrects the metabolic acidosis of the dialysis patient.

Another subject of this invention relates to multicomponent systems for preparation of the ready-to-use dialysis solutions described above. The preparation is preferably performed in a manner that is described in detail, i.e., by following the corresponding instructions (protocol). Said preparation may be performed manually, e.g., by mixing individual components or diluting one component with water. However, the preparation may also be performed automatically, e.g., by using a device that is suitable for this process and may be available commercially. The preparation need not necessarily lead to a dialysis solution with a static composition (remaining the same) but instead may also lead to a dialysis solution that undergoes continuous changes in its composition, where this change can be monitored by a suitable device. For example, the inventive polysaccharide may be present in a dialysis solution, which is diluted continuously during the dialysis treatment, so that the patient is exposed to a decreasing polysaccharide concentration.

In a preferred embodiment, the inventive dialysis solutions are suitable for use in the treatment of renal failure.

In another preferred embodiment, the inventive dialysis solutions are suitable for use in a dialysis treatment.

In another preferred embodiment, the inventive dialysis solutions are suitable for use in hemodialysis and/or peritoneal dialysis treatment.

Another subject of this invention relates to a kit, which is configured for preparation of the inventive dialysis solutions, where the kit comprises
    a first component,
    a second component and
    optionally one or more other components,
and the inventive dialysis solution is prepared by mixing the first component with the second component and optionally the additional component(s).

The kit comprises at least a first component and a second component. The kit may also comprise additional components, e.g., a third and a fourth component. The kit preferably consists of two components, which are preferably different from one another.

In the sense of this invention, the term "component" comprises liquid, semisolid or solid compositions, which may be the same as or different from one another, where the inventive ready-to-use dialysis solution is obtained by mixing all the components of the kit. A single component preferably contains a portion of the ingredients that are present in the ready-to-use dialysis solution.

The first and second components, independently of one another, may be solid, semisolid or liquid. If the components are liquid, they may be solutions or dispersions (e.g., dispersions or suspensions).

In a preferred embodiment, the first component is liquid, preferably pure water or an aqueous solution, and the second component is also liquid. In another preferred embodiment, the first component is liquid, preferably pure water or an aqueous solution, and the second component is solid, preferably a powdered mixture.

The first component is preferably a solution, containing osmotically active substances (e.g., the inventive polysaccharide), calcium ions, magnesium ions, hydronium ions and chloride ions.

The inventive kit may be designed in various ways. For example, the individual components may be present in separate containers (e.g., individual bags). However, the inventive kit is preferably a container such as a multi-chamber container system (e.g., a flexible or rigid multi-chamber container system), preferably a flexible multi-chamber bag system.

The inventive kit is preferably a multi-chamber container system, which contains the first component, the second component and optionally one or more additional components in chambers, which are separated from one another by detachable and/or breakable separation systems (e.g., breakable separating parts), where the first component, the second component and optionally the one or more additional components can be mixed with one another after releasing and/or breaking the separation system in order to obtain the inventive dialysis solution.

The multi-chamber container may be in the form of a plastic container (e.g., multi-chamber plastic bag), which has a separate chamber for each individual component. The plastic container preferably contains the individual component solutions in chambers separated from one another by partition elements.

The multi-chamber container is preferably a two-chamber bag comprising a plastic container having a first chamber and a second chamber, where the chambers may be separated from one another by a detachable and/or breakable separation system, and the first chamber contains the first component and the second chamber contains the second component. The release and/or breaking of the separation system results in the two components being mixed and forms the ready-to-use dialysis solution. The first chamber and the second chamber are preferably arranged adjacent to one another in the container and are separated from one another by the separation system. The separation system is preferably a separation seam (e.g., a detachable or breakable weld). The separation seam is preferably opened by applying a pressure to one of the chambers, whereupon the separation seam breaks and/or separates and the contents of the two chambers become mixed and the mixture can be used as a ready-to-use dialysis solution in dialysis treatment.

The first component of the inventive kit is preferably a sterile solution, which contains an acid and has a pH of ≤6.0; the second component is preferably also a sterile solution, which preferably contains a buffer and has a pH of ≥7.0.

The inventive polysaccharide may be contained in the first component or in the second component as well as in the two components in the same or different concentrations. In a preferred embodiment, the inventive polysaccharide is contained only in the first (acid) component. In another preferred embodiment, the inventive polysaccharide is contained only in the second (basic) component. The first component and/or the second component and/or the other optional component(s) may contain one or more electrolytes as well as a buffer.

Those skilled in the art will recognize that mixing of the individual components usually involves a dilution effect for the case when the components contain the ingredients in different concentrations. For example, if the inventive polysaccharide is contained exclusively in one of the components, then mixing of this component with at least one other component results in an increase in volume with respect to the amount of the inventive polysaccharide that is present and thus leads to a dilution, i.e., a decline in the polysaccharide concentration; consequently, the component preferably contains the inventive polysaccharide in a higher concentration than the ready-to-use dialysis solution.

The concentration of the inventive polysaccharide in the component is preferably close to the saturation concentration at a temperature of 5° C. in order to ensure a sufficient stability in storage at elevated temperatures.

In a preferred embodiment, the total mass concentration of inventive polysaccharide in the component is 0.01 g/L to 1.0 kg/L, more preferably 0.1 to 750 g/L, even more preferably 1.0 to 500 g/L, most preferably 10 to 250 g/L and in particular 100 to 200 g/L. In another preferred embodiment, the total mass concentration of inventive polysaccharide in the component is 25±24 g/L, more preferably 25±20 g/L, even more preferably 25±15 g/L, most preferably 25±10 g/L and in particular 25±5 g/L. In another preferred embodiment, the total mass concentration of inventive polysaccharide in the component is 50±25 g/L, more preferably 50±20 g/L, even more preferably 50±15 g/L, most preferably 50±10 g/L and in particular 50±5 g/L. In another preferred embodiment, the total mass concentration of inventive polysaccharide in the component is 75±25 g/L, more preferably 75±20 g/L, even more preferably 75±15 g/L, most preferably 75±10 g/L and in particular 75±5 g/L. In another preferred embodiment, the total mass concentration of inventive polysaccharide in the component is 100±25 g/L, more preferably 100±20 g/L, even more preferably 100±15 g/L, most preferably 100±10 g/L and in particular 100±5 g/L. In another preferred embodiment, the total mass concentration of inventive polysaccharide in the component is 200±25 g/L, more preferably 200±20 g/L, even more preferably 200±15 g/L, most preferably 200±10 g/L and in particular 200±5 g/L.

In a preferred embodiment, the second component contains the total amount of inventive polysaccharide and a suitable buffer, which adjusts the pH of the second component to more than 7.0, more preferably to more than 7.5, even more preferably to more than 8.0, most preferably to more than 8.5 and in particular to more than 9.0. This can preferably be achieved with bicarbonate, which may be present in the form of dissociated sodium bicarbonate and/or potassium bicarbonate. In another preferred embodiment, the second component is solid and comprises a powdered mixture containing at least one inventive polysaccharide and at least one buffer, e.g., sodium and/or potassium bicarbonate.

The multi-chamber bag is preferably suitable for the preparation of a dialysis solution, which may be used in the peritoneal dialysis treatment, and which contains the following ingredients, preferably in the following concentrations:

| | |
|---|---|
| $Ca^{2\oplus}$ | 0.5 to 5 meq/L; |
| $Mg^{2\oplus}$ | 0 to 3.0 meq/L; |
| $Cl^{\ominus}$ | 90.5 to 121 meq/L; |
| $K^{\oplus}$ | 0 to 4.0 meq/L; |
| $HCO_3^{\ominus}$ | 25 to 40 meq/L; | where one chamber of the multi-chamber bag system contains a first acid concentrate and another chamber contains a second basic concentrate; where the acid concentrate contains $Ca^{2\oplus}$ ions and the basic concentrate contains $HCO_3^{\ominus}$ ions but no $Ca^{2\oplus}$ ions; and the two concentrates can be mixed together after releasing and/or breaking the separation system (e.g., separation seam); where the mixing of the two concentrates leads to the preparation of the ready-to-use dialysis solution and the pH of the ready-to-use dialysis solution is 7.0 to 7.6.

The basic concentrate preferably contains at least one inventive polysaccharide and optionally glucose and/or polyglucose, whereas the acid concentrate does not contain any inventive polysaccharide or any glucose and/or polyglucose.

The basic concentrate preferably contains a quantity of bicarbonate, which leads to a bicarbonate concentration of the ready-to-use dialysis solution of at least 20 mM. The bicarbonate concentration of the basic component is preferably so high that the ready-to-use dialysis solution has a bicarbonate concentration of 25 mM.

The pH of the basic, buffered second concentrate is preferably adjusted with hydrochloric acid.

The two concentrates are preferably mixed together in a volume ratio of 10:1 to 1:10 or 8:1 to 1:8, more preferably 5:1 to 1:5 or 3:1 to 1:3, even more preferably 2:1 to 1:2 and in particular 1:1.

The multi-chamber bag preferably has a gas barrier film, which prevents gaseous $CO_2$ from escaping from the system. Those skilled in the art are familiar with gas barrier films.

A more preferred subject of this invention relates to a method for preparing a dialysis solution, in which the desired mixing ratio is adjusted automatically by a dialysis machine or a peritoneal dialysis cycler.

In a preferred embodiment, the invention relates to a solid composition which is suitable for preparing the inventive dialysis solution by dissolving it in a defined volume of a solvent (e.g., water). The solid composition is preferably a component described above and is thus a component of the inventive kit.

The solid composition contains the inventive polysaccharide in any solid form, e.g., as a powder, granules, pellets, etc. The inventive polysaccharide may be in the form of a lyophilisate or may be spray-dried.

The inventive solid composition preferably contains a bicarbonate salt, such as sodium or potassium bicarbonate. Das substance quantity ratio of bicarbonate to the inventive polysaccharide in the solid composition is preferably 1:100 to 100:1, more preferably 1:50 to 50:1, even more preferably 1:25 to 25:1, most preferably 1:10 to 10:1 and in particular 1:5 to 5:1.

The defined volume of solvent, which is required to prepare the inventive dialysis solution by dissolving the solid composition is preferably 1.0 to 2000 liters. The solvent is preferably purified water, sterilized water or water for injection purposes, which may optionally contain one or more of the electrolytes described above, one or more osmotically active substances (e.g., at least one inventive polysaccharide) and/or one or more of the buffers described above.

Another subject of this invention relates to the use of at least one inventive polysaccharide for preparation of the inventive dialysis solution (hemodialysis solution or peritoneal dialysis solution).

Another subject of this invention relates to the use of an inventive kit for preparation of the inventive dialysis solution (hemodialysis solution or peritoneal dialysis solution).

Another subject of this invention relates to the use of an inventive solid composition for preparation of the inventive dialysis solution (hemodialysis solution or peritoneal dialysis solution).

EXAMPLES

Example 1

Figure 2:
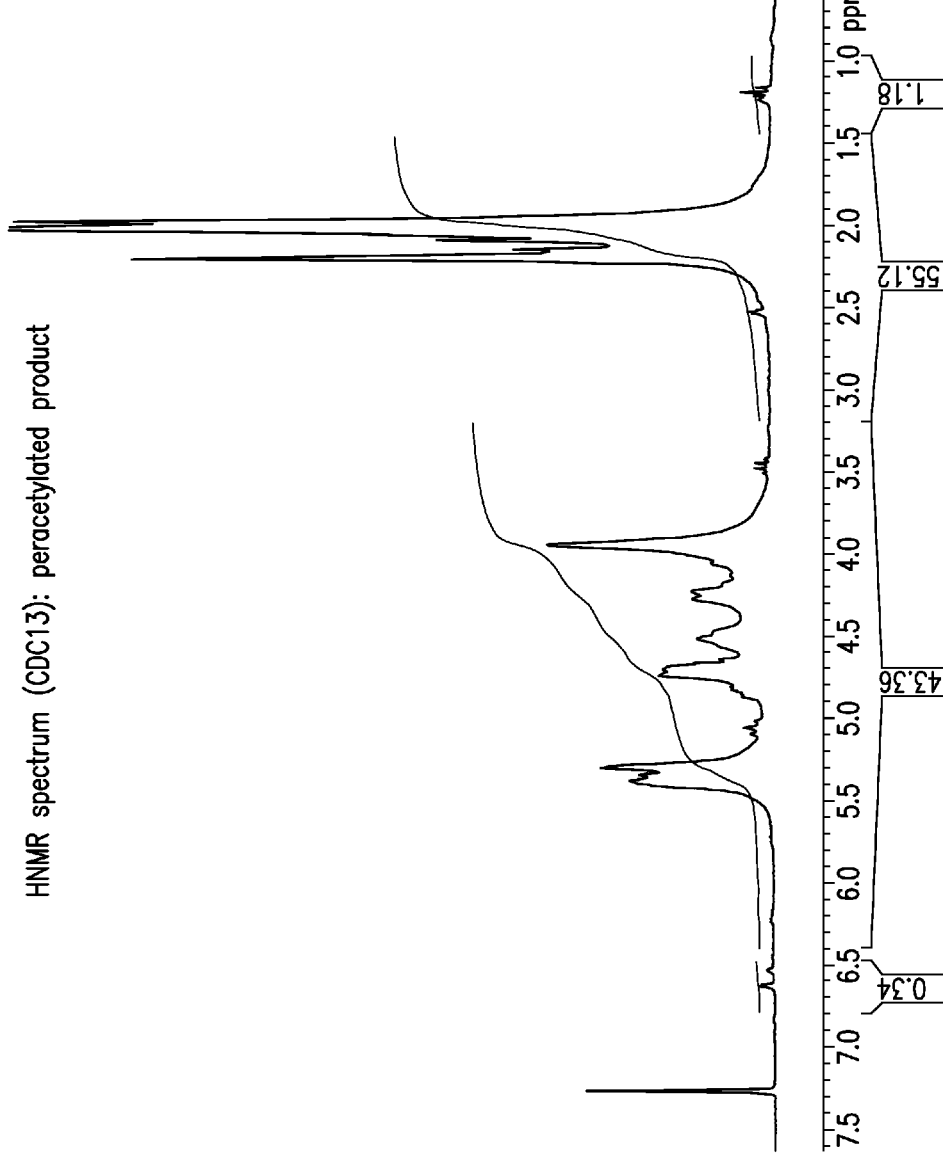
FIG. 2 is a graph showing an HNMR spectrum.

50 g degraded starch is dissolved in 500 mL DMSO. After dissolving the starch, one spatula tip of DMAP and 22.7 g maleic acid anhydride are added (0.75 mol/AGU). The mixture is stirred for 5 hours at 40° C. The product is precipitated in acetone with subsequent filtration and drying in vacuo at 40° C. HNMR and CNMR spectra were recorded (see FIG. 1 and FIG. 2): degree of substitution less than 0.1.

Example 2

60 g dried degraded starch (0.370 mol) is dissolved in 600 mL dried dimethylacetamide. After dissolving the starch, one spatula tip of DMAP, 37.2 g triethylamine and 36.36 g maleic acid anhydride are added. The mixture is stirred for 5 hours at 60° C. The product is precipitated in acetone with subsequent filtration and drying in vacuo at 40° C. HNMR and CNMR spectra were recorded.

Example 3

Like Example 2, but without the addition of triethylamine.

The inventive starch maleates thereby obtained have an increased osmolality in comparison with the unsubstituted degraded starch at the same concentration (determined experimentally based on the reduction in freezing point) and a greatly elevated colloid osmotic pressure and ultrafiltration.

Example 4

In a comparative experiment a filling volume of 10 ml of an osmotic agent with a concentration of 5% (m/m) in a matrix solution of 1 mmol/l $Ca^{2+}$, 0.5 mmol/l $Mg^{2+}$, 138 mmol/l $Na^+$, 106 mmol/l $Cl^-$ and 35 mmol/l lactate was filled into a semipermeable tube (regenerated cellulose, MWCO: 1000, Fa. Roth) and stirred in a bath of the same matrix solution for 24 hours at a temperature of 38° C. At various points of time the filling volume of the tube was measured reflecting the osmotic power of the agent.

As osmotic agents 2 starch maleates according to the invention were compared to glucose and Icodextrin as established osmotic agents. The starch maleates used had the following structure:

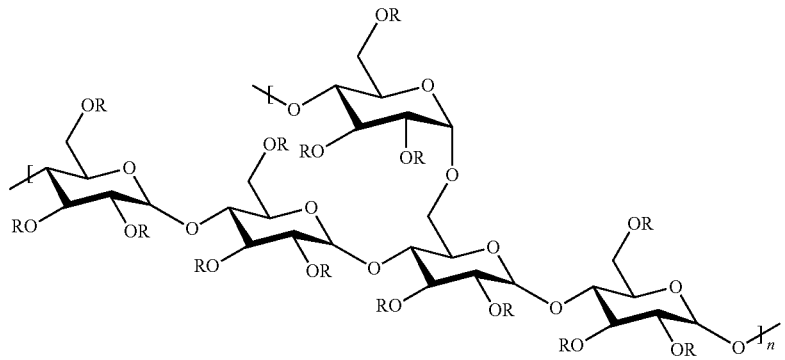

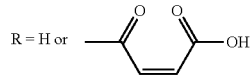

The two starch maleated differed in the degree of substitution (DS) while starch maleate 1 had a DS of 0.1, starch maleate 2 had a DS of 0.5.

Figure 3:
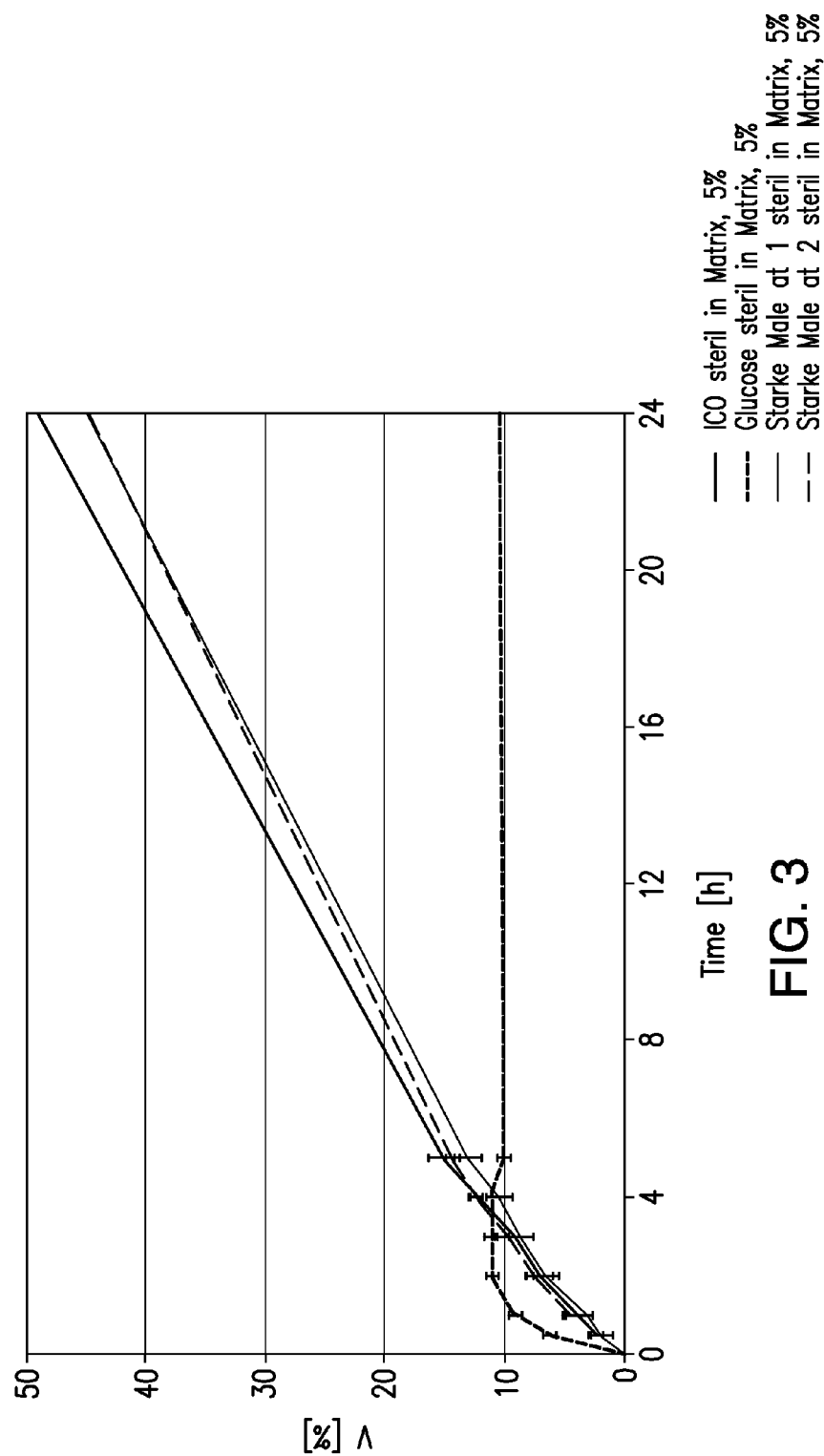
FIG. 3 is a diagram showing the results of a comparative experiment involving an osmotic agent in various matrix solutions.

The results are shown in FIG. 3 as a diagram.

The starch maleates showed an increased osmotic effect over glucose after a time period of 4 hours. They showed a slightly decreased osmotic effect compared to icodextrin.

What is claimed is:

1. A kit configured for the preparation of a dialysis solution, the kit comprising:
   a multi-chamber plastic bag comprising a first chamber and a second chamber, wherein the first chamber is separated from said second chamber by a detachable and/or breakable separation system;
   a solid composition comprising a starch in solid form contained in the first chamber; and
   a second component comprising a solvent, the second component contained in the second chamber;
   wherein the dialysis solution is obtained by mixing the solid composition with the second component, the solid composition then being dissolved by said solvent, wherein the solid composition is mixable with the second component after releasing and/or breaking the separation system, thus forming the dialysis solution, and
   wherein the starch is esterified at least partially with a citric acid or isocitric acid and wherein the obtained dialysis solution contains the starch esterified at least partially with a citric acid or isocitric acid in a total concentration of 0.001 mM to 10 M.

2. The kit according to claim 1, wherein the average molecular weight of the starch is between 2000 and 30,000 g/mol.

3. The kit according to claim 1, wherein the starch comprises a polysaccharide having a degree of polymerization between 10 and 170.

4. The kit according to claim 1, wherein a 7.5 weight percent aqueous solution of the starch has an osmolarity greater than 11.9 mosm/L.

5. The kit according to claim 1, wherein the starch comprises a polysaccharide having a degree of substitution between 0.01 and 3.

6. The kit according to claim 1, wherein the dialysis solution is suitable for hemodialysis or peritoneal dialysis treatment.

7. The kit of claim 1, further comprising one or more additional components, wherein the dialysis solution is obtained by mixing the solid composition with the second component and with the additional component(s).

* * * * *